US012765749B2

(12) United States Patent
Minakuchi et al.

(10) Patent No.: US 12,765,749 B2
(45) Date of Patent: Oct. 20, 2026

(54) ENDOSCOPE AND ENDOSCOPE SYSTEM

(71) Applicant: HOYA CORPORATION, Tokyo (JP)

(72) Inventors: Tadashi Minakuchi, Tokyo (JP); Toshiki Watanabe, Tokyo (JP)

(73) Assignee: PENTAX Medical Corporation, Tokyo (JP)

( * ) Notice: Subject to any disclaimer, the term of this patent is extended or adjusted under 35 U.S.C. 154(b) by 334 days.

(21) Appl. No.: 18/272,404

(22) PCT Filed: Oct. 5, 2021

(86) PCT No.: PCT/JP2021/036759
§ 371 (c)(1),
(2) Date: Jul. 14, 2023

(87) PCT Pub. No.: WO2022/153622
PCT Pub. Date: Jul. 21, 2022

(65) Prior Publication Data

US 2024/0130606 A1 Apr. 25, 2024
US 2024/0225421 A9 Jul. 11, 2024

(30) Foreign Application Priority Data

Jan. 15, 2021 (JP) ................................ 2021-004636

(51) Int. Cl.
*A61B 1/00* (2006.01)
*H01B 7/00* (2006.01)
*H01B 7/22* (2006.01)
*H01B 1/02* (2006.01)

(52) U.S. Cl.
CPC ...... *A61B 1/00114* (2013.01); *A61B 1/00124* (2013.01); *H01B 7/0009* (2013.01); *H01B 7/225* (2013.01); *H01B 1/026* (2013.01)

(58) Field of Classification Search
CPC ............ A61B 1/00114; A61B 1/00124; A61B 1/00018; A61B 1/00064; A61B 1/00078;
(Continued)

(56) References Cited

U.S. PATENT DOCUMENTS 5,876,326 A 3/1999 Takamura et al.
10,446,292 B2 10/2019 Ning et al.
(Continued)

FOREIGN PATENT DOCUMENTS

EP 0730844 A1 * 9/1996 ........... H01R 13/719
JP H06285018 A * 10/1994
(Continued)

OTHER PUBLICATIONS

Notice of Reasons for Refusal issued in Japanese Patent Application No. 2021-004636, dated Jan. 15, 2025, along with an English translation thereof.
(Continued)

*Primary Examiner* — Michael J Carey
*Assistant Examiner* — Christen A. Sharpless
(74) *Attorney, Agent, or Firm* — GREENBLUM & BERNSTEIN, P.L.C.

(57) ABSTRACT

An endoscope cable includes a plurality of individual cables, and is provided with an entire shield portion including a metal wire group having an electric shield function to surround entirety of the plurality of individual cables, and a cable core wire including a metal wire group in each of the individual cables. The metal wire group in at least one of the entire shield portion and the cable core wires is configured by combining a plurality of types of metal wires having different compositions from each other.

11 Claims, 5 Drawing Sheets

(58) Field of Classification Search
CPC .... A61B 1/0055; H01B 7/0009; H01B 7/225; H01B 1/026; G02B 23/2476
See application file for complete search history.

(56) References Cited

U.S. PATENT DOCUMENTS

| | | | | |
|---|---|---|---|---|
| 2012/0292079 | A1 | 11/2012 | Muramatsu et al. | |
| 2015/0195961 | A1 | 7/2015 | Yanagihara et al. | |
| 2017/0100018 | A1* | 4/2017 | Saito | G02B 23/24 |
| 2018/0151272 | A1* | 5/2018 | Watanabe | H01B 7/048 |
| 2019/0304633 | A1 | 10/2019 | Watanabe et al. | |
| 2022/0238253 | A1* | 7/2022 | Matsumura | H01B 7/295 |

FOREIGN PATENT DOCUMENTS

| | | | | |
|---|---|---|---|---|
| JP | H07184852 | A * | 7/1995 | |
| JP | H08256974 | A * | 10/1996 | A61B 1/00124 |
| JP | 2001-126552 | A | 5/2001 | |
| JP | 2004195269 | A * | 7/2004 | |
| JP | 2013-176567 | A | 9/2013 | |
| JP | 2014-071974 | A | 4/2014 | |
| JP | 2018-085302 | A | 5/2018 | |
| JP | 2019-500727 | A | 1/2019 | |
| JP | 2019-0175781 | A | 10/2019 | |
| WO | 2016/076314 | A1 | 5/2016 | |

OTHER PUBLICATIONS

European Search Report issued in European application No. 21919513.8, dated Oct. 29, 2024.

International Search Report issued in WIPO Patent Application No. PCT/JP2021/036759, dated Dec. 21, 2021, along with an English translation thereof.

* cited by examiner

ENDOSCOPE AND ENDOSCOPE SYSTEM

TECHNICAL FIELD

The present invention relates to an endoscope inserted into a body cavity and an endoscope system.

BACKGROUND ART

An endoscope is a device that is inserted into a body cavity of a human body or the like and observes a living tissue on an inner surface of the body cavity. The endoscope includes an endoscope cable that electrically connects a distal tip portion of the endoscope to be inserted into the body cavity and a connector located at a rear end portion of the endoscope, the connector being to be connected to a processor for an endoscope. In the endoscope cable, an image sensor provided at the distal tip portion of the endoscope transmits an instruction signal for instructing an imaging operation from the processor for an endoscope, and transmits an image signal for transmitting a captured image signal to the endoscope class processor. Furthermore, in a case where an LED light source element is provided at the distal tip portion in addition to the image sensor provided at the distal tip portion, the endoscope cable transmits a control signal for controlling a power line for supplying power to the LED light source element and controlling on and off of light emission of the LED light source element.

Since the distal tip portion of the endoscope is inserted into the body cavity of a subject, it is desirable that the distal tip portion be made as thin as possible in order to alleviate pain of the subject. For this purpose, the built-in endoscope cable favorably has a small outer diameter.

Meanwhile, since a passage in the body cavity is bent or curved, the endoscope cable is required to be flexibly bent. Moreover, to avoid disconnection of transmission lines such as signal lines and power lines, it is also required for the endoscope cable to secure durability so that the endoscope cable is not damaged or broken even when the endoscope cable is repeatedly bent and stretched.

Furthermore, the endoscope cable includes a shield portion in which a shield line is disposed so as to surround a conductive wire such as the transmission line that transmits the instruction signal, the control signal, or the image signal, in order to block noise from the outside from the internal conductive wire or to prevent noise from the internal conductive wire from leaking to the outside.

To secure durability in such an endoscope cable, a structure is known in which a highly rigid wire material (copper alloy) is used for each portion of a conductor used in the endoscope cable, or a wire diameter of an external conductive wire constituting the shield portion is different from a wire diameter of an internal conductive wire that is the signal line, that is, a core wire (see JP 10-33471 A). With this structure, it is possible to improve tensile resistance strength, cyclic bending strength, and cyclic torsional strength.

SUMMARY OF INVENTION

Technical Problem

The endoscope cable having the above structure can secure the durability such as the tensile resistance strength, cyclic bending strength, and cyclic torsional strength. However, in a case of performing connection work to remove a cover (insulator) that covers a periphery of the core wire of the endoscope cable and connecting the core wire to each element and a port of a connector, there is a problem that the connection work cannot be sufficiently efficiently performed because of insufficient pliability of the endoscope cable. If a composition of the wires constituting the core wire and the shield portion is changed in order to secure the pliability of the endoscope cable, the durability may not be sufficiently secured. As described above, it is not possible to sufficiently achieve both the durability of the endoscope cable and easiness of work such as the connection work.

Therefore, an object of the present invention is to enable both the durability of an endoscope cable and the easiness of work such as connection work in an endoscope having the endoscope cable that electrically connects a distal tip portion of the endoscope to be inserted into a body cavity and a connector located at a rear end portion of the endoscope, the connector being to be connected to a processor for an endoscope.

Solution to Problem

An aspect of the present disclosure is an endoscope including an endoscope cable that electrically connects a distal tip portion of the endoscope to be inserted into the body cavity, and a connector located at a rear end portion of the endoscope, the connector being to be connected to a processor for an endoscope.

The endoscope cable includes a plurality of individual cables, and is provided with an entire shield portion including a metal wire group having an electric shield function to surround entirety of the plurality of individual cables, and a cable core wire including a metal wire group in each of the individual cables.

The metal wire group in at least one of the entire shield portion and the cable core wires is configured by combining a plurality of types of metal wires having different compositions from each other.

It is favorable that at least one of the plurality of individual cables includes an individual cable shield portion including a metal wire group having an electric shield function so as to surround a periphery of the cable core wire.

It is favorable that the metal wire group in the individual cable shield portion is configured by combining a plurality of types of metal wires having different compositions from each other.

It is favorable that the metal wire groups in at least two of the entire shield portion, the cable core wire, and the individual cable shield portion are configured by combining a plurality of types of metal wires having different compositions from each other, and the types of metal wires used for the metal wire groups in the at least two are same, but a ratio of a number of the plurality of types of metal wires used in the metal wire group is different between the metal wire groups in the at least two.

It is favorable that the metal wire group in at least one of the entire shield portion and the individual cables is arranged along a periphery of the endoscope cable or along a periphery of the individual cable such that the plurality of types of metal wires is repeated in a predetermined order.

Another aspect of the present disclosure is also an endoscope including an endoscope cable that electrically connects a distal tip portion of the endoscope to be inserted into the body cavity, and a connector located at a rear end portion of the endoscope, the connector being to be connected to a processor for an endoscope.

The endoscope cable includes a plurality of individual cables, and is provided with an entire shield portion including a metal wire group having an electric shield function to surround entirety of the plurality of individual cables, and a cable core wire including a metal wire group in each of the individual cables.

At least one of the plurality of individual cables includes an individual cable shield portion including a metal wire group having an electric shield function so as to surround a periphery of the cable core wire.

A combination of types of metal wires used for the metal wire group is different between the metal wire groups in at least two of the entire shield portion, the cable core wire, and the individual cable shield portion.

It is favorable that the metal composition is different among the plurality of types of metal wires.

It is favorable that the plurality of types of metal wires includes at least a soft copper (conforming to JIS C3102-1984 or JIS C3152-1984) wire and a copper alloy wire having a Young's modulus larger than the soft copper wire.

It is favorable that the copper alloy wire includes a plurality of types of copper alloy wires having different metal compositions.

It is favorable that at least one characteristic of conductivity (JIS C3002) and Young's modulus is different among the plurality of types of metal wires having different compositions.

According to still another aspect of the present disclosure is an endoscope system including: the endoscope; and a processor for an endoscope that is connected to the endoscope via the connector, outputs an instruction signal to the endoscope, and performs signal processing in response to an input of a signal output from the endoscope.

The endoscope is an endoscope selected from an endoscope group connectable to the processor for an endoscope according to use conditions including a site in a body cavity into which the endoscope is inserted and operation content of the endoscope.

At least one of a combination of types of the metal wires used for the endoscope cable or a ratio of a number of the plurality of types of metal wires used in the metal wire group is different in at least two endoscopes in the endoscope group according to the use conditions.

Advantageous Effects of Invention

According to the above-described endoscope, it is possible to achieve both the durability of the endoscope cable and the easiness of work such as connection work.

DESCRIPTION OF EMBODIMENTS

Hereinafter, an endoscope and an endoscope system according to embodiments will be described with reference to the drawings.

Figure 1:
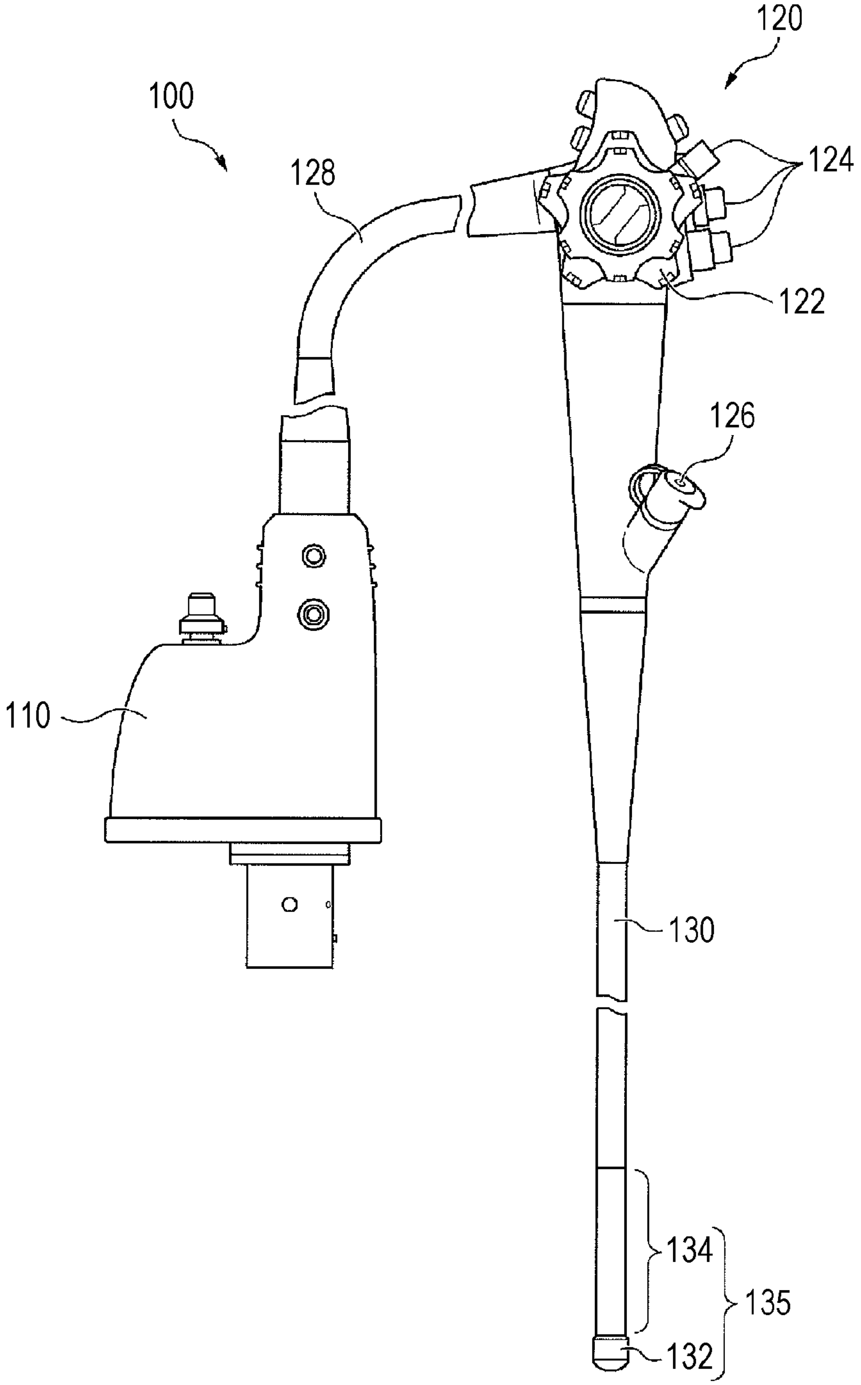
FIG. 1 is an external perspective view of an endoscope according to an embodiment.
Figure 2:
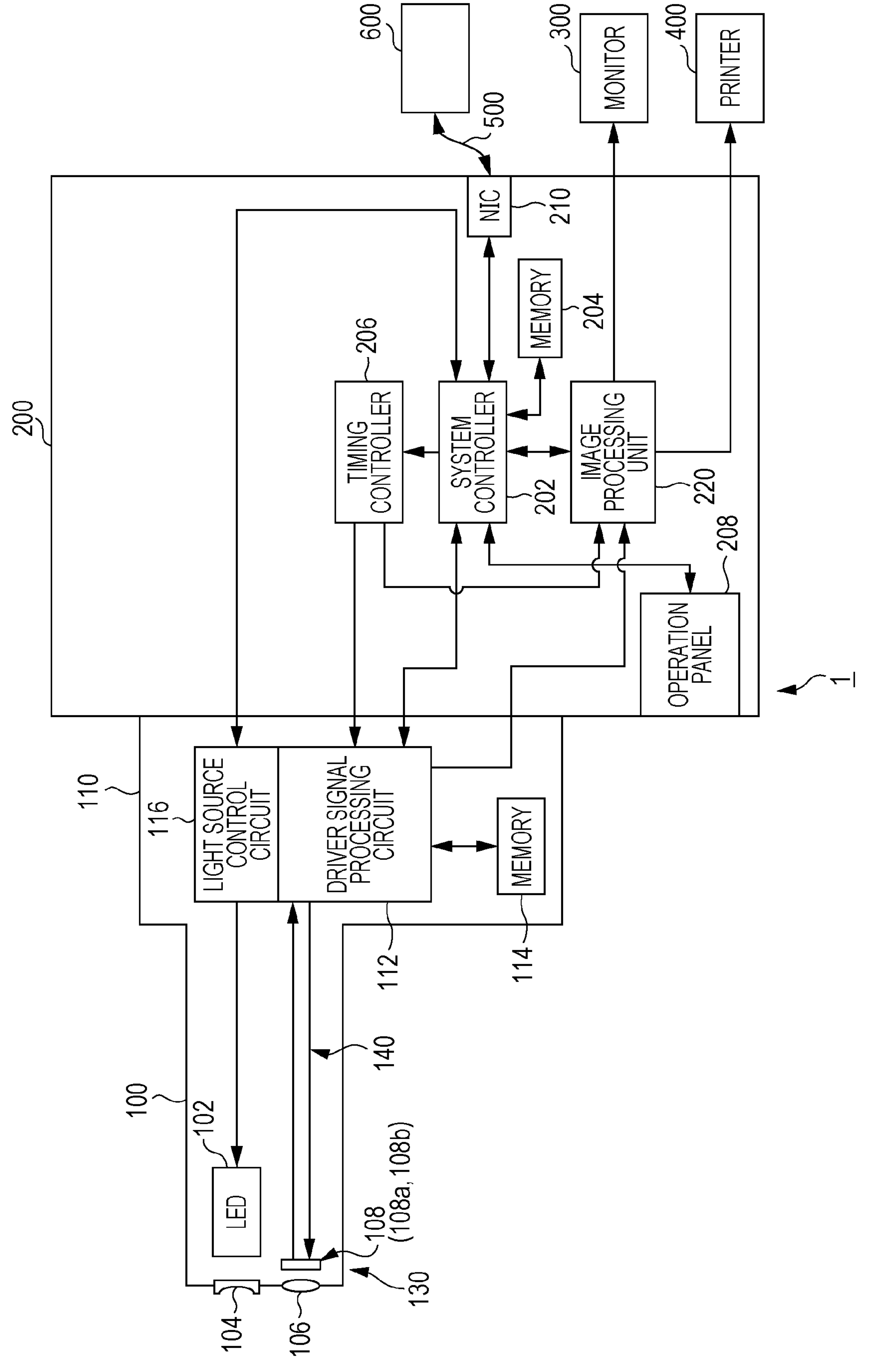
FIG. 2 is a block diagram illustrating a configuration of an endoscope system according to an embodiment.

FIG. 1 is an external perspective view of an endoscope according to an embodiment. FIG. 2 is a block diagram illustrating a configuration of an endoscope system according to an embodiment.

An endoscope cable 140 (see FIGS. 3 to 6) to be described below achieves both durability and easiness of work such as connection work, and a metal wire group configured in at least one of an entire shield portion 160 (see FIGS. 3 to 6) and cable core wires 142 to 152 (see FIGS. 3 to 6) included in the endoscope cable 140 is configured by combining a plurality of types of metal wires having different compositions from each other. Thereby, it is possible to achieve both the durability and the easiness of work such as connection work required for the endoscope cable 140.

Here, the durability can be evaluated by applying stress to the endoscope cable 140 by the following tests and counting the number of disconnections of the metal wire:

- a simple torsion test in which the endoscope cable 140 is repeatedly axially rotated around an axis of the endoscope cable a predetermined number of times at a predetermined angle;
- a simple curve test (JIS C3005 4.27);
- a curved torsion test in which the simple torsion test and the simple curve test are simultaneously performed;
- a kink resistance test (loop tensile test) in which the endoscope cable 140 is looped and pulled; and
- a twisting test (JIS C3005 4.30).

An endoscope system 1 illustrated in FIG. 2 is a system specialized for medical use, and mainly includes an endoscope 100, a processor 200 for an electronic endoscope, and a monitor 300. Each of the endoscope 100 and the monitor 300 is connected to a processor 200.

As illustrated in FIG. 1, the endoscope 100 includes a connector 110 and an operation unit 120, and further includes a flexible cable 130 extending forward from the operation unit 120 and having flexibility, a distal tip portion 132 and a bending tube 134 provided in front of the flexible cable 130, and a universal tube 128 extending rearward from the operation unit 120. The connector 110 is fixed to a rear end of the universal tube 128 and is configured to be connected to the processor 200.

The universal tube 128 and the flexible cable 130 are provided with an endoscope cable that electrically connects the distal tip portion 132 and the connector 110.

A plurality of bending operation wires is inserted into the operation unit 120, the flexible cable 130, and the bending tube 134, a distal tip of each bending operation wire is connected to an end of the bending tube 134. A rear end of each bending operation wire is connected to a bending operation knob 122 of the operation unit 120. The bending tube 134 is bent at any angle in any direction according to the operation of the bending operation knob 122.

Moreover, the operation unit 120 includes a plurality of operation buttons 124. A function to perform each operation is allocated to the operation button 124 such that the distal tip portion 132 performs each operation by pressing the operation button 124. Examples of the above operation include an operation of discharging a liquid or a gas from an air/water supply port (not illustrated) of the distal tip portion 132 to a living tissue that is a capture object, an operation of discharging a cleaning liquid supplied to the distal tip portion 132 via the flexible cable 130 from a cleaning liquid discharge nozzle (not illustrated) of the distal tip portion 132 toward an objective lens 106 provided in the distal tip portion 132 to clean a surface of the objective lens 106, and an operation of sucking a liquid or a gas in the living tissue from a suction port (not illustrated) provided in the distal tip portion 132 and discharging the sucked liquid or gas to an outside.

In this manner, the operation performed at the distal tip portion 132 can be operated by pressing the operation button 124.

Moreover, a forceps insertion port 126 is provided in the operation unit 120 on a side of the distal tip portion 132. The forceps insertion port 126 is connected to a forceps port of the distal tip portion 132 via a tube in the flexible cable 130. Therefore, a pair of forceps inserted through the forceps insertion port 126 and guided to the forceps port of the distal tip portion 132 can be taken out through the forceps port and treat the living tissue.

The distal tip of the bending tube 134 is provided with the distal tip portion 132. The distal tip portion 132 is configured by a hard resin material that is not substantially elastically deformed, and a light distribution lens 104 is provided on a distal tip surface of the distal tip portion 132 as an emission window of illumination light for illuminating the living tissue, and the objective lens 106 is further provided as an observation window.

Inside the distal tip portion 132, an LED light source 102 and an image sensor 108 located immediately behind the objective lens 106 are provided. That is, the distal tip portion 132 provided at the distal tip of the elongated flexible cable 130 includes the LED light source 102, the light distribution lens 104, the objective lens 106, and the image sensor 108. The objective lens 106 is provided on a front surface of the image sensor 108, and forms an image of the living tissue on a light receiving surface of the image sensor 108 in a visual field range of a predetermined visual field angle.

In the example illustrated in FIG. 2, the LED light source 102 is provided in the distal tip portion 132, but the LED light source 102 may be provided in the processor 200. In this case, an optical guide cable is used in which a plurality of optical fiber cables for transmitting the illumination light is bundled, the optical guide cables extending from the processor 200 to the distal tip portion 132 via the connector 110. In addition, instead of the LED light source 102, a light source device that emits illumination light of each color according to characteristics of an optical filter using a white light source lamp and the optical filter may be used.

The flexible cable 130, the bending tube 134, and the distal tip portion 132 form an insertion portion 135 that is inserted into the body cavity. An image signal line extending from the image sensor 108 provided at the distal tip portion 132 extends from the distal tip portion 132 to the inside of the connector 110 through the inside of the bending tube 134, the flexible cable 130, the operation unit 120, and the universal tube 128. The connector 110 is connected to the processor 200. The processor 200 processes an image signal transmitted from the image sensor and controls an image of the object captured by the image sensor 108 to be displayed on the monitor 300.

As illustrated in FIG. 2, the processor 200 of the endoscope system 1 includes a system controller 202 and a timing controller 206. The system controller 202 executes various programs stored in a memory 204 and integrally controls the entire electronic endoscope system 1. In addition, the system controller 202 changes various settings of the electronic endoscope system 1 according to an instruction from a user (operator or assistant) input to an operation panel 208.

The timing controller 206 outputs a clock pulse for adjusting operation timing of each unit to each circuit in the electronic endoscope system 1.

In such a configuration, in the endoscope system 1, a display image is created in the following flow.

The light emitted from the LED light source 102 is emitted as the illumination light to the living tissue, which is the object, via the light distribution lens 104. Reflected light from the living tissue forms an optical image on the light receiving surface of the image sensor 108 via the objective lens 106.

The image sensor 108 is, for example, a single-plate color charge-coupled device (CCD) image sensor in which various filters such as an infrared (IR) cut filter 108*a* and a Bayer-arrayed color filter 108*b* are arranged on the light receiving surface, and generates primary color signals of red (R), green (G), and blue (B) according to the optical image formed on the light receiving surface. Instead of the single-plate color CCD image sensor, a single-plate color complementary metal oxide semiconductor (CMOS) image sensor can also be used. In this way, the endoscope 100 images the living tissue inside an organ and generates a moving image signal, using the image sensor 108.

A driver signal processing circuit 112 is provided inside the connector 110 of the endoscope 100. The driver signal processing circuit 112 applies predetermined signal processing such as color interpolation and matrix calculation to the moving image signal input from the image sensor 108 to generate image signals (luminance signal Y and color difference signals Cb and Cr), and outputs the generated image signals to an image processing unit 220 of the processor 200 for an electronic endoscope. Furthermore, the driver signal processing circuit 112 accesses a memory 114 and reads specific information of the endoscope 100. The specific information of the endoscope 100 recorded in the memory 114 includes, for example, the number of pixels, sensitivity, an operable frame rate, and a model number of the image sensor 108. The driver signal processing circuit 112 outputs the specific information read from the memory 114 to the system controller 202.

The system controller 202 performs various calculations on the basis of the information stored in the memory 204 and the specific information of the endoscope 100, and generates a control signal. The system controller 202 uses the generated control signal to control the operation and timing of each circuit in the processor 200 for an electronic endoscope such that processing suitable for the endoscope 100 being connected to the processor 200 for an electronic endoscope is performed.

The timing controller 206 supplies a clock pulse to the driver signal processing circuit 112, the image processing unit 220, and a light source unit 230 according to the timing control by the system controller 202. The driver signal processing circuit 112 performs driving control of the image sensor 108 at timing synchronized with the frame rate of a video image processed on the side of the processor 200 for an electronic endoscope in accordance with the clock pulses supplied from the timing controller 206.

The image processing unit 220 applies set image processing to the captured image of the living tissue, and outputs the image to the monitor 300 as a moving image. Furthermore, the image processing unit 220 may apply processing to the image so that a lesion site can be easily diagnosed. For example, the image processing unit 220 applies processing with an emphasized feature capable of distinguishing the lesion site and a healthy site to the image and outputs information obtained by quantifying the degree of progress of the lesion site to the monitor 300.

In addition, the image processing unit 220 outputs an image obtained by extracting a part of the moving image as a still image and the information obtained by quantifying the degree of progress of the lesion site to a printer 400.

Specifically, under the control of the system controller 202, the image processing unit 220 generates a video signal for displaying an image or the like on a monitor on the basis of the image signal input from the driver signal processing circuit 112, and outputs the video signal to the monitor 300. Moreover, the image processing unit 220 performs, for the image of the living tissue obtained by the endoscope 100, quantification processing for quantifying a feature amount of each pixel of the image in which the lesion site can be distinguished from the healthy site and evaluates the degree of progress of the lesion site of the image, and further generates a color map image obtained by replacing a numerical value of each pixel obtained by the quantification processing with a color. The image processing unit 220 generates a video signal for displaying information of a result of the quantification processing and the color map image on a monitor, and outputs the video signal to the monitor 300. As a result, the user can accurately perform an examination through the image displayed on a display screen of the monitor 300. The image processing unit 220 outputs the image, the information of the result of the quantification processing, and the color map image to the printer 400 as necessary.

The processor 200 is connected to a server 600 via a network interface card (NIC) 210 and a network 500. The processor 200 can download information regarding an examination using the endoscope (for example, electronic health record information of a patient and information of a practitioner) from the server 600. The downloaded information is displayed on, for example, the display screen of the monitor 300 and the operation panel 208. In addition, the processor 200 can cause the server 600 to store an examination result by uploading the examination result by the endoscope 100 to the server 600.

The endoscope 100 illustrated in FIGS. 1 and 2 is an example in which the image sensor 108 is provided in the distal tip portion 132, but the distal tip portion 132 may be provided with an ultrasound transducer together with the image sensor 108. In this case, the endoscope cable 140 is provided with a transmission line for transmitting a signal from the ultrasound transducer as an individual cable.

In the universal tube 128 and the flexible cable 130 of the endoscope 100, the endoscope cable 140 that electrically connects the distal tip portion 132 of the endoscope to be inserted into the body cavity and the connector 110 located at the rear end portion of the endoscope 100, the connector being to be connected to the processor 200, is provided.

In FIG. 2, the endoscope cable 140 includes two transmission lines illustrated with two arrow solid lines, the transmission lines connecting the driver signal processing circuit 112 and the image sensor 108, and one transmission line for transmitting a light source control signal, the transmission line connecting the light source control circuit 116 and the LED light source 102. FIG. 2 illustrates a mode in which the endoscope cable 140 includes the three transmission lines as individual cables for the sake of simplicity, but may include four or more multiple individual cables.

Figure 3:
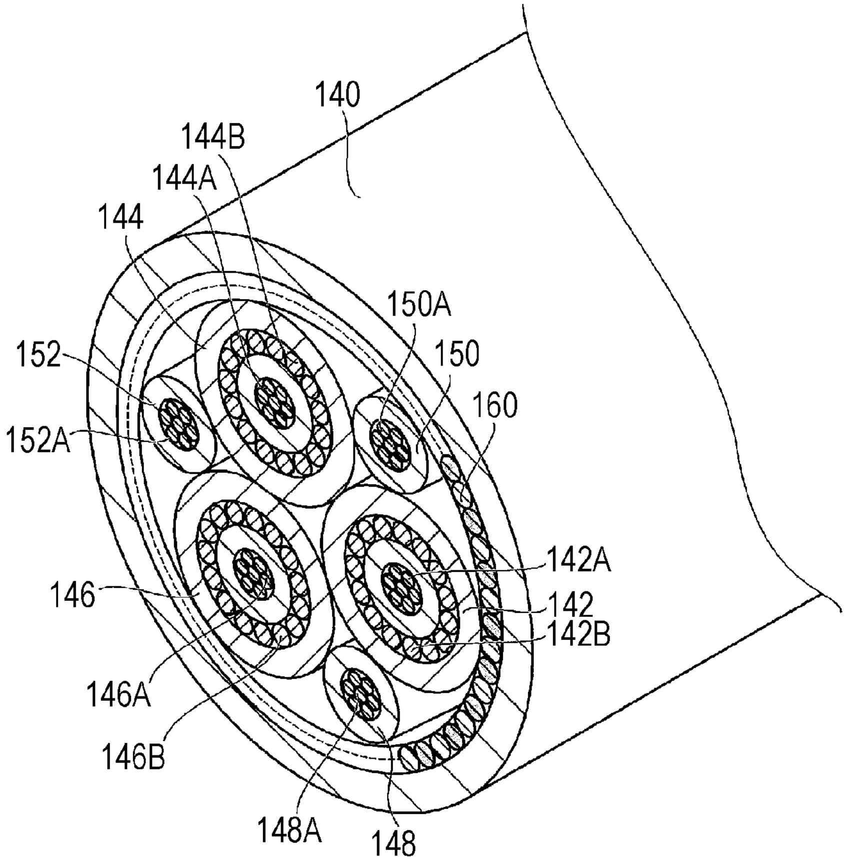
FIG. 3 is a view for describing an example of an endoscope cable used for an endoscope according to an embodiment.

FIG. 3 is a view for describing an example of the endoscope cable 140.

The endoscope cable 140 includes a plurality of individual cables. In FIG. 3, the six individual cables 142 to 152 are included. The endoscope cable 140 includes the entire shield portion 160 including the metal wire group having the electric shield function to surround the entire individual cables 142 to 152, and includes cable core wires 142A to 152A each including the metal wire group in the respective individual cables 142 to 152.

The metal wire group in the entire shield portion 160 is configured by combining a plurality of types of metal wires having different compositions from each other. Note that the surface of the metal wire may be plated with tin, silver, or the like.

In the example illustrated in FIG. 3, the entire shield portion 160 is configured by combining a plurality of types of metal wires having different compositions from each other in the metal wire group. However, in another example, the cable core wires 142A to 152A may be configured by combining a plurality of types of metal wires having different compositions from each other in the metal wire groups. Further, the entire shield portion 160 and at least one of the cable core wires 142A to 152A may be configured by combining a plurality of types of metal wires having different compositions from each other in the metal wire groups.

In the example illustrated in FIG. 3, in the entire shield portion 160, the metal wire group having a circular cross section is arranged along a circumference. Specifically, the metal wire having a cross section in white and the metal wire having a cross section in gray are alternately arranged so as to be adjacent to each other along the circumference. That is, in the entire shield portion 160, two types of metal wires are arranged in order.

Figure 4:
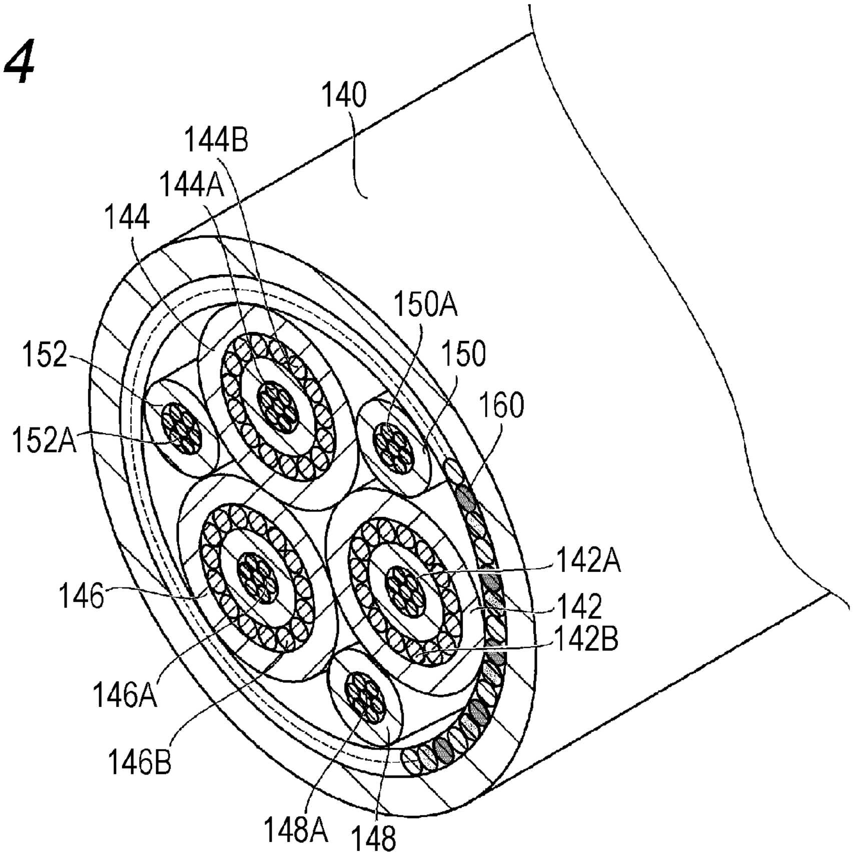
FIG. 4 is a view for describing another example of the endoscope cable used for an endoscope according to an embodiment.

FIG. 4 is a view for describing another example of the endoscope cable 140. In the example illustrated in FIG. 4, the metal wire group having a circular cross section is arranged along the circumference in the entire shield portion 160, similarly to FIG. 3. However, the metal wire having a cross section in white, the metal wire having a cross section in light gray, and the metal wire having a cross section in dark gray as the types of metal wires are arranged in order. That is, in the entire shield portion 160, three types of metal wires are arranged in order.

Figure 5:
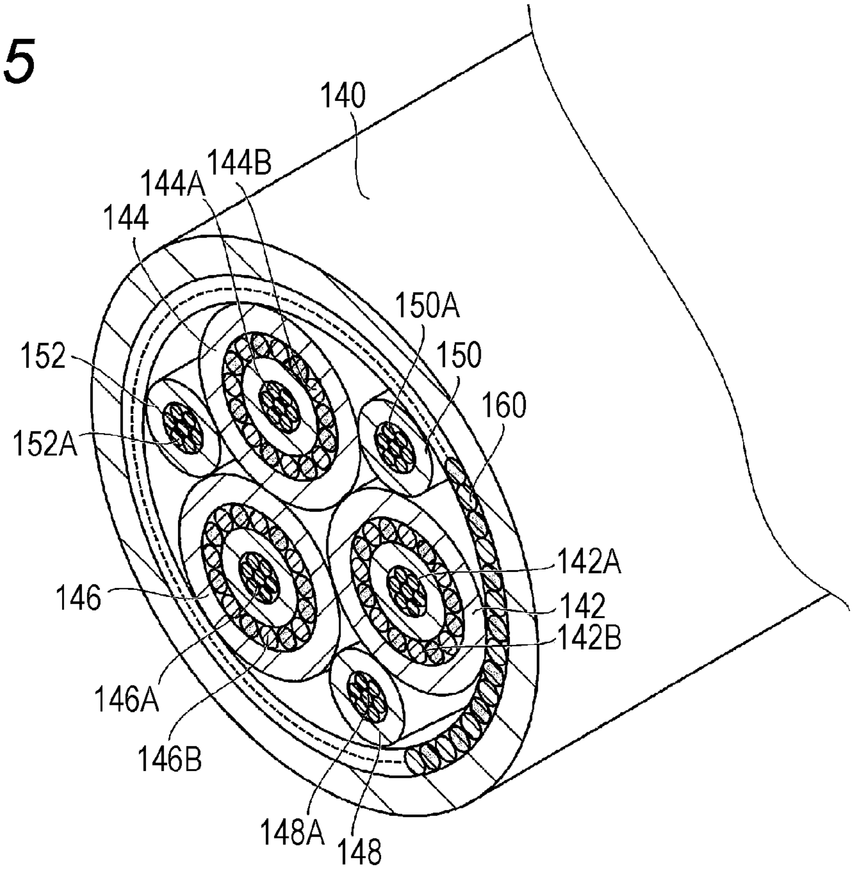
FIG. 5 is a view for describing another example of the endoscope cable used for an endoscope according to an embodiment.

FIG. 5 is a view for describing another example of the endoscope cable 140. In the example illustrated in FIG. 5, the metal wire group having a circular cross section is arranged along the circumference in the entire shield portion 160, similarly to FIG. 3, and the metal wire having a cross section in white and the metal wire having a cross section in gray as the types of metal wires are arranged in order. Such two types of metal wires are arranged not only in the entire shield portion 160 but also in the metal wire groups of individual cable shield portions 142B, 144B, and 146B of the individual cables 142, 144, and 146.

Figure 6:
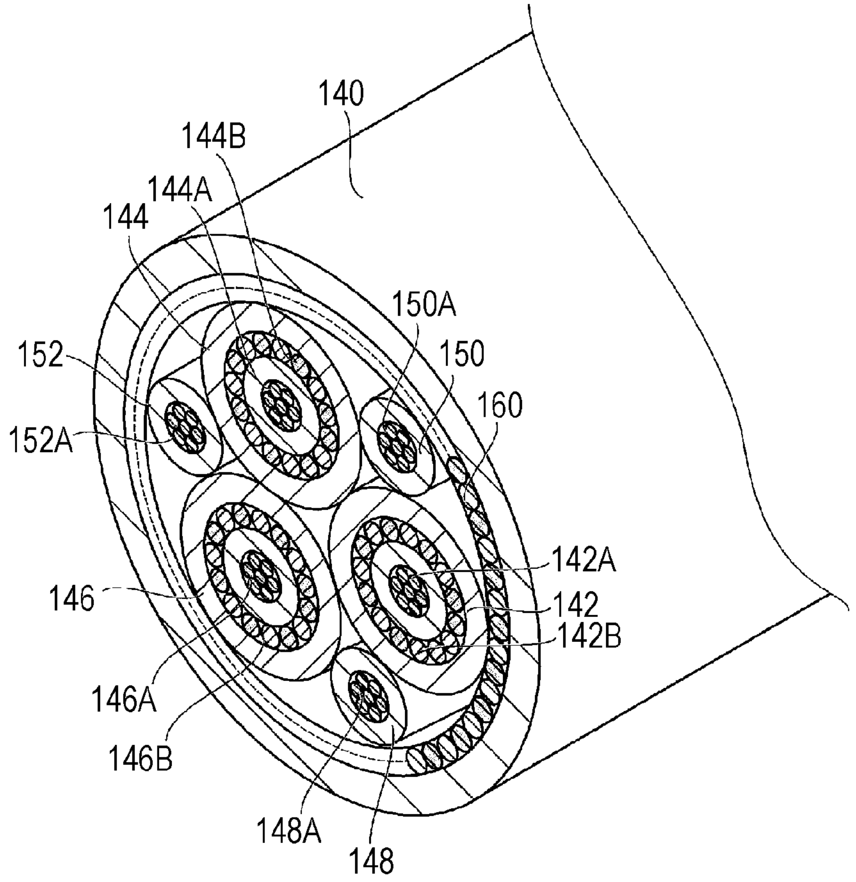
FIG. 6 is a view for describing another example of the endoscope cable used for an endoscope according to an embodiment.

FIG. 6 is a view for describing still another example of the endoscope cable 140. In the example illustrated in FIG. 6, the metal wire group having a circular cross section is arranged along the circumference in the entire shield portion 160, similarly to FIG. 3, and the metal wire having a cross section in white and the metal wire having a cross section in gray as the types of metal wires are arranged in order. Such two types of metal wires are arranged not only in the entire shield portion 160 but also in the metal wire groups of the cable core wires 142A to 152A and the individual cable shield portions 142B to 146B of the individual cables 142 to 152.

As described above, in the present embodiment, the plurality of types of metal wires is arranged in the entire shield portion 160 and/or the cable core wires 142A to 152A and the like of the individual cables 142 to 152. That is, the metal wire group in at least one of the entire shield portion 160 and the cable core wires 142A to 152A is configured by combining a plurality of types of metal wires having different compositions from each other.

By configuring the endoscope cable 140 using such a metal wire group, it becomes possible to achieve both the durability of the endoscope cable and easiness of work such as connection work. In general, the durability and a repulsive force against deformation are often different among a plurality of different types of metal wires. Since the metal wire having excellent durability has a large repulsive force against deformation, in a case where the cable core wires 142A to 152A are exposed at the end of the endoscope cable 140 and the metal wires are twisted to be connected to a terminal of the image sensor 108 by solder or the like, the connection work becomes difficult due to the large repulsive force, and the efficiency of the connection work may be reduced. On the other hand, in the metal wire having a small repulsive force against deformation, the efficiency of the connection work is improved, but the metal wire is easily disconnected by handling such as twisting, bending, or pulling of the endoscope cable 140, that is, the durability is reduced. Therefore, the metal wire group in at least one of the entire shield portion 160 and the cable core wires 142A to 152A is configured by combining a plurality of types of metal wires having different compositions from each other.

Further, it is favorable that at least one of the plurality of individual cables 142 to 152 includes the individual cable shield portion including the metal wire group having the electric shield function so as to surround the periphery of the cable core wire. The individual cable having such a configuration can block electromagnetic waves from the outside, and can suppress the electromagnetic waves generated by a high-frequency signal flowing through the cable core wire from leaking to the outside. It is favorable that such a metal wire group in the individual cable shield portion is configured by combining a plurality of types of metal wires having different compositions from each other. Thereby, it becomes possible to achieve both the durability of the endoscope cable and the easiness of work such as connection work.

Note that the above-described embodiment has adopted the mode of combining a plurality of types of metal wires for one metal wire group. However, the metal wire groups in at least two of the entire shield portion 160, the cable core wires 142A to 152A, and the individual cable shield portions 142B, 144B, and 146B may be configured by combining a plurality of types of metal wires having different compositions from each other, and the types of metal wires used for the metal wire groups in the at least two are same, but a ratio of a number of the plurality of types of metal wires used in the metal wire group may be different between the metal wire groups in the at least two. By changing the ratio of the number of the plurality of types of metal wires used, it is possible to achieve both the durability and the efficiency of connection work in the endoscope cable 140 while adjusting the above-described number according to characteristics (for example, conductivity and electromagnetic shielding properties) required for each of the cable core wires 142A to 152A and the individual cable shield portions 142B, 144B, and 146B of the individual cables 142 to 152, and the entire shield portion 160.

Note that it is favorable that the metal wire group in at least one of the entire shield portion 160 and the individual cables 142 to 152 is arranged along the periphery of the endoscope cable or along the periphery of the individual cable such that the plurality of types of metal wires is repeated in a predetermined order. In the case of the two types of metal wires as illustrated in FIGS. 3, 5, and 6, the metal wires are alternately arranged. Further, in the case of the three types of metal wires as illustrated in FIG. 4, the three types of metal wires are repeatedly arranged in order. Note that, in the case of changing the ratio of the number of metal wires used, it is favorable that different types of metal wires are regularly and repeatedly arranged.

A combination of the types of metal wires used for the metal wire group may be different between the metal wire groups in at least two of the entire shield portion 160, the cable core wires 142A to 152A, and the individual cable shield portions 142B, 144B, and 146B. For example, in the metal wire group in the entire shield portion 160, a metal wire A and a metal wire B are combined, whereas in one metal wire group of the cable core wires 142A to 152A, the metal wire A and a metal wire C are combined. In addition, the number of types of metal wires used for the metal wire group may be different between at least two metal wire groups.

The plurality of types of metal wires has different compositions. The phrase "have different compositions" includes that the metal compositions are different, for example, the metal compositions constituting an alloy are different in a case where the metal wire is made of the alloy, and that a composition ratio of metal components is different even if the same metal components are included. In addition, it is also possible to form a wire in which the metal component and the composition ratio are the same but physical characteristics are different due to a change in crystal structure depending on metal production conditions (thermal treatment and the like) even if the metal component and the composition ratio are the same. The phrase "have different compositions" also includes those having different physical characteristics due to a change in crystal structure even if the composition ratio is the same.

According to an embodiment, it is favorable that the plurality of types of metal wires includes at least a soft copper (conforming to JIS C3102-1984 or JIS C3152-1984) wire and a copper alloy wire having a Young's modulus larger than the soft copper wire. Since the soft copper wire has high conductivity and a small repulsive force against deformation, the soft copper wire has excellent electrical characteristics as the cable core wires 142A to 152A, and the efficiency of connection work is improved. However, the soft copper wire is easily disconnected by twisting, bending, or pulling the endoscope cable 140. That is, the durability is low. In contrast, since various types of copper alloy wires generally have lower conductivity than the soft copper wire and have a large repulsive force against deformation, the electrical characteristics as the cable core wires 142A to 152A are low and the efficiency of connection work is low, whereas the durability is excellent. Therefore, by combining the soft copper wire and the copper alloy wire having a Young's modulus larger than the soft copper wire and using them for one metal wire group, it becomes possible to achieve both the durability and the efficiency of connection work.

Note that it is favorable that the copper alloy wire includes a plurality of types of copper alloy wires having different metal compositions. The having different metal compositions includes a case where the composition ratio is different even if the composition components are the same, in addition to the case where the composition components are different, as described above.

It is favorable that at least one characteristic of the conductivity (JIS C3002) and the Young's modulus is different among the plurality of types of metal wires having different compositions. As a result, it is possible to achieve both the durability and the efficiency of connection work in the endoscope cable 140 while satisfying the electrical characteristics required for the individual cables 142 to 152.

Note that the metal wires of the entire shield portion 160 and the individual cable shield portions 142B to 146B may be configured in a horizontal winding structure or a braided structure.

When the distal tip portion 132 of the endoscope 100 is inserted into the body cavity of the human body, the endoscope cable 140 receives stress such as being bent, twisted, or pulled so as to follow a bent tube in the body cavity. Since the endoscope cable 140 receives the above-described stress many times every time the endoscope 100 is used, the endoscope cable 140 is required to have excellent durability as described above. It is favorable that the endoscope 100 is selected from a plurality of endoscopes according to use conditions including the site in the body cavity to which the endoscope 100 is inserted and the operation content of the endoscope instead of using the same endoscope regardless of the site in the body cavity to be examined. Therefore, the endoscope system 1 favorably includes a plurality of the endoscopes 100 connectable to the processor 200 for an endoscope. Therefore, in this case, the endoscope 100 to be used is an endoscope selected from an endoscope group connectable to the processor 200 according to the use conditions including the inspection site in the body cavity and the operation content of the endoscope 100.

At this time, it is favorable that at least one of the combination of the types of metal wires used for the endoscope cable 140 or the ratio of the number of the plurality of types of metal wires used in the metal wire group is different in at least two endoscopes in the endoscope group according to the use conditions. Since the stress applied to the endoscope cable 140 varies depending on the use conditions, it is sufficient to secure the durability according to the stress. For example, in a case of imaging a site with many bends such as a large intestine, the endoscope cable 140 having excellent durability is used. Meanwhile, in the case of the endoscope 100 that performs ultrasound diagnosis, an output signal level is small, and thus the electrical characteristics in the endoscope cable 140 are the most prioritized characteristics. In this case, the endoscope cable 140 using the metal wire having low conductivity for the cable core wires 142A to 152A, or having excellent electromagnetic shielding properties in order not to be affected by external noise.

The endoscope and the endoscope system according to the embodiments of the present invention have been described in detail, but the present invention is not limited to the above-described embodiment. As a matter of course, various improvements or modifications may be made within the scope not departing from the concept of the present invention.

The present invention relates to a patent application of Japanese Patent Application No. 2021-004636 filed with the Japan Patent Office on Jan. 15, 2021, the entire contents of which are incorporated herein by reference.

The invention claimed is:

1. An endoscope, to be inserted into a body cavity, comprising:

a distal tip portion;

an endoscope cable that electrically connects the distal tip portion; and a connector located at a rear end portion of the endoscope, the connector being configured to be connected to a processor for an endoscope, wherein the endoscope cable includes a plurality of individual cables, and is provided with an entire shield portion including a metal wire group having a circular cross section arranged along a circumference of the endoscope cable so as to surround entirety of the plurality of individual cables and comprising a plurality of metal wires arranged together to provide an electric shield function, and a cable core wire including a metal wire group in each of the individual cables, the metal wire group of the entire shield portion is configured in a horizontal winding structure surrounding the entirety of the plurality of individual cables, the metal wire group in at least one of the entire shield portion and the cable core wires comprises a plurality of types of metal wires having different compositions from each other, and adjacent metal wires arranged along the circumference of the entire shield portion alternately including: a first type of metal wire having higher durability and higher repulsive force against deformation, and a second type of metal wire having lower repulsive force against deformation to improve connection workability such that deformation resistance and connection workability are balanced in the entire shield portion.

2. The endoscope according to claim 1, wherein at least one of the plurality of individual cables includes an individual cable shield portion including a metal wire group having an electric shield function so as to surround a periphery of the cable core wire.

3. The endoscope according to claim 2, wherein the metal wire group in the individual cable shield portion is configured by combining a plurality of types of metal wires having different compositions from each other.

4. The endoscope according to claim 2, wherein the metal wire groups in at least two of the entire shield portion, the cable core wire, and the individual cable shield portion are configured by combining a plurality of types of metal wires having different compositions from each other, and the types of metal wires used for the metal wire groups in the at least two are same, but a ratio of a number of the plurality of types of metal wires used in the metal wire group is different between the metal wire groups in the at least two.

5. The endoscope according to claim 1, wherein the metal wire group in at least one of the entire shield portion and the individual cables is arranged along a periphery of the endoscope cable or along a periphery of the individual cable such that the plurality of types of metal wires is repeated in a predetermined order.

6. An endoscope, to be inserted into a body cavity, comprising: a distal tip portion;

an endoscope cable that electrically connects the distal tip portion; and a connector located at a rear end portion of the endoscope, the connector being to be connected to a processor for an endoscope, wherein the endoscope cable includes a plurality of individual cables, and is provided with an entire shield portion including a metal wire group having a circular cross section arranged along a circumference of the endoscope cable so as to surround entirety of the plurality of individual cables and comprising a plurality of metal wires arranged together to provide an electric shield function, and a cable core wire including a metal wire group in each of the individual cables, at least one of the plurality of individual cables includes an individual cable shield portion including a metal wire group having an electric shield function so as to surround a periphery of the cable core wire, the metal wire group of the entire shield portion is configured in a horizontal winding structure surrounding the entirety of the plurality of individual cables, a combination of types of metal wires used for the metal wire group is different between the metal wire groups in at least two of the entire shield portion, the cable core wire, and the individual cable shield portion, and adjacent metal wires arranged along the circumference of the entire shield portion alternately including: a first type of metal wire having higher durability and higher repulsive force against deformation, and a second type of metal wire having lower repulsive force against deformation to improve connection workability such that deformation resistance and connection workability are balanced in the entire shield portion.

7. The endoscope according to claim 1, wherein a metal composition is different among the plurality of types of metal wires.

8. The endoscope according to claim 1, wherein the plurality of types of metal wires includes at least a soft copper (conforming to JIS C3102-1984 or JIS C3152-1984) wire and a copper alloy wire having a Young's modulus larger than the soft copper wire.

9. The endoscope according to claim 8, wherein the copper alloy wire includes a plurality of types of copper alloy wires having different metal compositions.

10. The endoscope according to claim 1, wherein at least one characteristic of conductivity (JIS C3002) and Young's modulus is different among the plurality of types of metal wires having different compositions.

11. An endoscope system comprising:

the endoscope according to claim 1; and a processor for an endoscope that is connected to the endoscope via the connector, outputs an instruction signal to the endoscope, and performs signal processing in response to an input of a signal output from the endoscope, wherein the endoscope is an endoscope selected from an endoscope group connectable to the processor for an endoscope according to use conditions including a site in a body cavity into which the endoscope is inserted and operation content of the endoscope, and at least one of a combination of types of the metal wires used for the endoscope cable and a ratio of a number of the plurality of types of metal wires used in the metal wire group is different in at least two endoscopes in the endoscope group according to the use conditions.

* * * * *